(12) United States Patent
Larose et al.

(10) Patent No.: US 8,280,648 B2
(45) Date of Patent: Oct. 2, 2012

(54) METHOD FOR LOCATING THE APPEARANCE OF A DEFECT IN A MEDIUM USING A WAVE

(75) Inventors: Eric Francois Larose, Meylan (FR); Vincent Bruno Robert Rossetto-Giaccherino, Grenoble (FR)

(73) Assignee: Centre National de la Recherche Scientifique—CNRS, Paris Cedex (FR)

( * ) Notice: Subject to any disclaimer, the term of this patent is extended or adjusted under 35 U.S.C. 154(b) by 321 days.

(21) Appl. No.: 12/697,934

(22) Filed: Feb. 1, 2010

(65) Prior Publication Data
US 2010/0256928 A1 Oct. 7, 2010

(51) Int. Cl.
*G01B 5/02* (2006.01)
(52) U.S. Cl. .......................................................... 702/39
(58) Field of Classification Search ...................... 702/39
See application file for complete search history.

(56) References Cited

U.S. PATENT DOCUMENTS
5,588,032 A 12/1996 Johnson et al.

OTHER PUBLICATIONS

French Search Report of FR 09 50612 dated Sep. 17, 2009.
Bordier JM & AI: "The influence of multiple scattering in coherent ultrasonic inspection of coarse grain stainless steel", Dec. 8, 1991, cited in the French Search Report.
Margaret Cheney & AI: "Imaging that exploits multipath scattering from point scatterers; Imaging that exploits multipath scattering from point scatterers", Inverse problems, Institute of Physics Publishing, Oct. 1, 2004, cited in the French Search Report.
Margerin L. & AI: "Monte Carlo simulation of multiple scattering of elastic waves" Journal of Geophysical Research American Geophys. Union USA, Apr. 10, 2000, cited in the French Search Report.
Phanidhar Anugonda & AI, "Diffusion of ultrasound in concrete", Ultrasonics 39 (2001).
Richard Berkovits & AI, "Theory of Speckle-Pattern Tomography in Multiple-Scattering Media", Physical Review Letters, vol. 65, N° 25, Dec. 17, 1990.
F. Brenguier, "Postseismic Relaxation Along the San Andreas Fault at Parkfield from Continuous Seismological Observations", Sep. 12, 2008, vol. 321, Science.
M. L. Cowan, "Velocity Fluctuations in Fluidized Suspensions Probed by Ultrasonic Correlation Spectroscopy", vol. 85, No. 2 Physical Review Letters Jul. 10, 2000.
M. L. Cowan, "Diffusing acoustic wave spectroscopy", Physical Review E, vol. 65, 2002.
Shechao Feng, "Acoustical nondestructive evaluation of heterogeneous materials in the multiple scattering regime", J. Acoust. Soc. Am. 90(4), Pt. 1, Oct. 1991.

(Continued)

*Primary Examiner* — Tung S Lau
(74) *Attorney, Agent, or Firm* — Miller, Matthias & Hull LLP

(57) ABSTRACT

A medium is equipped with sources adapted for emitting a wave and sensors adapted for receiving the wave emitted. The method for locating an appearance of a defect in the medium comprises an initialization step in which reference impulse responses of the wave between the sources and sensors are determined, then at least one defect detection step in which the impulse responses of the wave between the sources and the sensors are measured, a decorrelation coefficient between the impulse responses and the reference impulse responses is calculated, a probability of exploration of a position is calculated, an error function for each source-sensor pair is calculated, and a product of at least some of the error functions of the source-sensor pairs is calculated. The product represents a map of a probability of the appearance of the defect at each position in the medium.

11 Claims, 2 Drawing Sheets

OTHER PUBLICATIONS

Thomas Gorin, "Dynamics of Loschmidt echoes and fidelity decay", Physics Reports 435 (2006) 33-156.

Alexandre Grêt, "Time-lapse monitoring of rock properties with coda wave interferometry", Journal of Geophysical Research, vol. 111, 2006.

M. Heckmeier & AI, "Visualization of °ow in multiple-scattering liquids", Europhys. Lett., 34 (4), pp. 257-262 (1996).

M. Heckmeier & AI, "Imaging of dynamic heterogeneities in multiple-scattering media", vol. 14, No. 1/Jan. 1997/J. Opt. Soc. Am. A.

Eric Larose & AI, "Observation of multiple scattering of kHz vibrations in a concrete structure and application to monitoring weak changes", Physical Review E 73, (2006).

Eric Larose & AI, "Monitoring stress related velocity variation in concrete with a 2.10-5 relative resolution using diffuse ultrasound", Monitoring weak changes in concrete, Jan. 9, 2009.

Valentin Leroy & AI, "Temperature-dependent diffusing acoustic wave spectroscopy with resonant scatterers", Physical Review E 77, (2008).

Yinghui Lu & AI, "A methodology for structural health monitoring with diffuse ultrasonic waves in the presence of temperature variations", Ultrasonics 43 (2005) 717-731.

Ludovic Margerin & AI, "Radiative transfer and diffusion of waves in a layered medium: new insight into coda Q", Geophys. J. Int. (1998) 134, 596-612.

Jennifer E. Michaels & AI, "Detection of Structural Damage from the Local Temporal Coherence of Diffuse Ultrasonic Signals", IEEE Transactions on Ultrasonics, Ferroelectrics, and Frequency Control, vol. 52, No. 10, Oct. 2005.

J. C. J. Paasschens & AI, "Solution of the time-dependent Boltzmann equation", Physical Review E vol. 56, No. 1 Jul. 1997.

D. J. Pine & AI, "Diffusion-Wave Spectroscopy", vol. 60, No. 12, Physical Review Letters, Mar. 21, 1998.

G. Poupinet & AI, "Monitoring Velocity Variations in the Crust Using Earthquake Doublets: An Application to the Calaveras Fault, California", Journal of Geophysical Research. vol. 89. No. B7, pp. 5719-5731, Jul. 10, 1984.

Roel Snieder & AI, "Coda Wave Interferometry for Estimating Nonlinear Behavior in Seismic Velocity", Science, vol. 295, Mar. 22, 2002.

Thesis of Cédric Payan, Caracterisation Non Destructive Du Beton. Etude Du Potentiel De L'acoustique Non Lineaire >>, Nov. 15, 2007.

C. Vannest & AI, "Non-Destructive Evaluations in Multiple-Scattering Media", Europhysics Letters., 24 (5), pp. 339-344, Nov. 10, 1993.

Richard L. Weaver & AI, "Temperature dependence of diffuse field phase", Ultrasonics 38 (2000), 491-494.

Richard L. Weaver & AI, "Coda-Wave Interferometry in Finite Solids: Recovery of P-to-S Conversion Rates in an Elastodynamic Billiard", Physical Review Letters, vol. 90, No. 25, Jun. 27, 2003.

Jens Becker & AI, "Characterization of Cement-Based Materials Using Diffuse Ultrasound", Journal of Engineering Mechanics, ASCE / Dec. 2003.

Yves Berthaud, "Damage Measurements in Concrete via an Ultrasonic Technique. Part I Experiment", Cement and Concrete Research, vol. 21, pp. 73-82, 1991.

Robert A. Guyer & AI, "Nonlinear Mesoscopic Elasticity: Evidence for a New Class of Materials", Physics Today, Apr. 30, 1999.

Eric N. Landis & AI, "Frequency-Dependent Stress Wave Attenuation in Cement-Based Materials", Journal of Engineering Mechanics, Jun. 1995.

D.M. McCann & AI, "Review of NDT methods in the assessment of concrete and masonry structures", NDT&E International 34 (2001) 71-84.

C. Payan & AI, "Applying nonlinear resonant ultrasound spectroscopy to improving thermal damage assessment in concrete", JASA Express Letters, Published Online Mar. 13, 2007.

T.P. Philippidis & AI, "Experimental study of wave dispersion and attenuation in concrete", Ultrasonics 43 (2005) 584-595.

John S. Popovics & AI, "A Survey of Developments in Ultrasonic NDE of Concrete", IEEE Transactions on Ultrasonics, Ferroelectrics, and Frequency Control, vol. 41, No. 1, Jan. 1994.

Kevin L. Rens & AI, "Bridge Management and Nondestructive Evaluation", Journal of Performance of Constructed Facilities ASCE, Feb. 2005.

Joseph A. Turner & AI, "Scattering of elastic waves in heterogeneous media with local isotropy", J. Acoust. Soc. Am. 109 (5), Pt. 1, May 2001.

Odile Abraham & AI, "Low-frequency impact-echo method used for detecting voids in prestressing ducts", Bulletin des Laboratoires des Ponts et Chaussées, 239, Jul.-Aug. 2002, Ref 4428, pp. 41-50.

Christophe Aubagnac & AI, "Evaluation of various non-destructive monitoring methods prior to post-failure analysis of a beam element on the Pont Neuf Bridge in Foix, France", Bulletin des Laboratoires des Ponts et Chaussées, 241, Nov.-Dec. 2002, Ref 4417, pp. 85-97.

METHOD FOR LOCATING THE APPEARANCE OF A DEFECT IN A MEDIUM USING A WAVE

CROSS-REFERENCE TO RELATED APPLICATIONS

This application claims priority under the Paris Convention to French Application No. 09 50612, filed on Jan. 30, 2009.

FIELD OF THE DISCLOSURE

The invention relates to a method for locating the appearance of a defect in a medium using a wave.

BACKGROUND OF THE DISCLOSURE

Methods for locating a defect are known in which the medium is equipped with:
- sources placed in said medium and adapted for emitting a wave in the medium, and
- sensors placed in said medium and adapted for receiving said emitted wave.

In particular, conventional imaging methods propagate acoustic or ultrasonic waves in a medium on different dates. Assuming that the propagation speed of the wave is known in the medium, it is possible to link a time to a distance and build up a reflectivity or reflectivity variation image at each point of the medium, showing the changes that have occurred between the two dates.

This type of method is effective for identifying heterogeneities or scatterers in a medium, when the wave is propagated in the medium in simple scattering regime, i.e. when, on its path, the wave only interacts with a single heterogeneity before being detected.

For a medium comprising numerous heterogeneities, such as concrete, the ultrasonic wave used in the aforementioned known method has a relatively low frequency of less than 50 kHz. However, when the detection of small defects included in such a heterogeneous medium is sought, this method is inefficient as the wavelength used is too large. Furthermore, the simple scattering regime method is not very sensitive as the ultrasonic wave only encounters the defect once on its path (travel) in the medium.

On the other hand, when the wave is propagated in the medium in multiple scattering regime in such a heterogeneous medium, i.e. when the wave interacts with several heterogeneities on its path before being detected, such a conventional imaging technique is no longer operational. It is no longer possible to associate a propagation time with a single path, nor to associate a path with a heterogeneity.

SUMMARY OF THE DISCLOSURE

The purpose of the present invention is in particular to overcome these drawbacks, and to allow in particular for the location of a defect in the multiple scattering regime.

To this end, a method for locating the appearance of defects comprises the following steps:
- an initialisation step in which reference impulse responses $h_{ref}(R,S,t)$ of the wave between the sources and the sensors are determined, then
- at least one defect detection step, in which:
a) impulse responses $h_i(R,S,t)$ of the wave between the sources and the sensors are measured on a date $t_i$, i being a positive natural number,
b) a decorrelation coefficient $K_i(S,R,t)$ between the impulse responses $h_i(R,S,t)$ on the date $t_i$ and the reference impulse responses $h_{ref}(R,S,t)$ is calculated,
c) a probability of exploration $P(S,R,t,x)$ of a position x of the medium by the acoustic wave is calculated,
d) an error function $e_i(S,R,x)$ for each source-sensor pair is calculated, and
e) the product $p(i,x)$ of at least some of the error functions $e_i(S,R,x)$ of the source-sensor pairs is calculated, by $$p(i,x) = \prod_{S,R} e_i(S,R,x),$$

said product $p(i,x)$ representing a map of the probability of the appearance of a defect U at each position x.

By means of these provisions, the method allows in particular for the location of small defects in a heterogeneous medium.

In various embodiments of the method according to the invention, one or more of the following provisions may be used:
- the medium comprises heterogeneities and the wave is propagated in the medium according to a multiple scattering regime for which the wave interacts with more than one heterogeneity on its path;
- after step e), the product $p(i,x)$ is normalised by dividing each value by Norm=$\int p(i,x) \cdot dx$, integral over all of the positions x of the medium;
- the reference impulse responses $h_{ref}(R,S,t)$ are determined by the mean of N impulse responses $h_j(R,S,t)$ on dates $t_j$, j being a natural number such that $0 \leq j < i$, and N being such that $1 \leq N \leq i$;
- between steps a) and b), the measured impulse responses $h_i(R,S,t)$ are corrected by replacing them with corrected impulse responses $h_i(R,S,t(1-\epsilon))$, where $\epsilon$ is a temporal expansion coefficient that maximises the following correlation coefficient:

$$CC(\varepsilon) = \frac{\int h_i(R,S,t(1-\varepsilon)) \cdot h_{ref}(R,S,t) \cdot dt}{\sqrt{\int h_i^2(R,S,t) \cdot dt \cdot \int h_{ref}^2(R,S,t) \cdot dt}};$$

- the decorrelation coefficient $K_i(S,R,t)$ is calculated using the following formula:

$$K_i(S,R,t) = 1 - \frac{\int_{t-T/2}^{t-T/2} h_i(R,S,t) \cdot h_{ref}(R,S,t) \cdot dt}{\sqrt{\int_{t-T/2}^{t+T/2} h_i^2(R,S,t) \cdot dt \cdot \int_{t-T/2}^{t+T/2} h_{ref}^2(R,S,t)}}$$

where T is a temporal parameter, such that between $t-T/2$ and $t+T/2$, there are several oscillations in the impulse response $h_i(R,S,t)$;
- the probability of exploration $P(S,R,t,x)$ of the position x to within dx is calculated using the following formula:

$$P(S,R,t,x) \cdot dx = \int_0^t \frac{g(x_S, x, u) \cdot g(x, x_R, t-u)}{g(x_S, x_R, t)} \cdot du$$

where $g(x_S,x,u)$ is the transport probability of the wave which, leaving the source at time zero, arrives at position x after a time u, $g(x,x_R,t-u)$ is the transport probability of the wave which, leaving position x at time zero, arrives at the sensor after a time t−u, $g(x_S,x_R,t)$ is the transport probability of the wave which, leaving the source at time zero, arrives at the sensor after a time t;

the error function $e_i(S,R,x)$ is calculated using the following formula:

$$e_i(S, R, x) = F\left(\frac{K_i(S, R, t) - P(S, R, t, x)}{\sigma}\right)$$

where

F is a positive, even and decreasing function between 0 and +∞,

σ is an assumed maximum error, $K_i$ is the decorrelation coefficient estimated by the impulse response measurements, and P is a probability of exploration of the position x by the wave;

when no more accurate determination of the function F exists, the Gaussian probability is used, and the error function $e_i(S,R,x)$ is then calculated using the following formula:

$$e_i(S, R, x) = \frac{1}{\sqrt{2\cdot\pi}\cdot\sigma} \cdot e^{-\frac{[K_i(S,R,t)-P(S,R,t,x)]^2}{2\sigma^2}}$$

where:

σ is an assumed maximum error, $K_i$ is the decorrelation coefficient estimated by the impulse response measurements, and P is a probability of exploration of the position x by the wave;

the medium is a composite building material;

the wave is an ultrasonic acoustic wave;

the ultrasonic acoustic wave has a frequency of more than 50 kHz.

Other characteristics and advantages of the invention will become apparent on reading the following description of one of its embodiments, given as a non-limitative example, with reference to the attached drawings.

DETAILED DESCRIPTION OF THE DISCLOSURE

The subject-matter of the invention is a method for detecting a defect U that appears over time in a medium 1 and for determining its position inside the medium 1.

The method uses:

a wave propagation in the multiple scattering regime, and a processing of the signals by Bayesian inversion, based on the comparison of a calculated or theoretical probability of disturbance of the wave linked to the appearance of a defect in a position and on a date, and the same probability measured or estimated by measurements of disturbance of the wave linked to the appearance of the defect in the same position.

By wave propagation is meant in particular any wave of the following types: acoustic wave, ultrasonic wave, microwave, elastic wave, seismic wave, electromagnetic wave and optical wave.

The following description of the method will therefore endeavour to present an embodiment in which defects are sought into a material such as concrete using ultrasonic waves. However, the method can be applied to numerous fields or applications other than non-destructive materials testing, such as seismology, radars, optics, etc.

Figure 1:
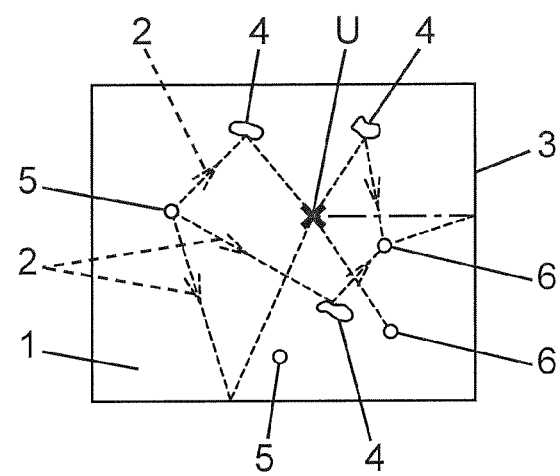
FIG. 1 is a diagram showing a medium, in which waves are propagated, according to the method of the invention.

As shown in FIG. 1, the medium 1 is constituted for example by a composite building material, such as concrete, and comprises:

sources 5, identified respectively by index-numbers S comprised between 1 and P, and placed in the medium 1 at known positions $x_S$, said sources 5 being adapted for emitting an ultrasonic wave 2 in the medium 1, sensors 6, identified respectively by index-numbers R comprised between 1 and Q, and placed in the medium 1 in known positions $x_R$, said sensors 6 being adapted for receiving said ultrasonic wave 2 emitted by at least one of the sources 5.

Positions $x_S$, $x_R$ must be understood as each being a vector representing the position of the source 5 and the sensor 6 respectively in a system of coordinates, for example Cartesian.

The sources 5 and sensors 6 are distributed in the volume of the medium 1 and/or around its periphery 3. The resolution of the method depends on the position and number of sources 5 and sensors 6.

If the medium 1 is made from concrete, the ultrasonic wave 2 has a scattering regime for a high frequency of the wave, i.e. for example greater than 50 kHz. In this propagation regime, the ultrasonic wave 2 undergoes multiple scatterings and travels along multiple paths in the medium 1, due to reflections off the periphery 3 of the medium or off heterogeneities or aggregate 4 included in the non-homogeneous concrete material of the medium 1.

Due to the scattering regime, the ultrasonic wave 2 interacts several times with the defect U, which enables the method to be more sensitive.

On implementation of this method, the impulse responses $h_i(R,S,t)$ of the ultrasonic wave between the sources 5 and the sensors 6 are measured on a date $t_i$, i being a positive or zero natural number representing this date $t_i$. R and S are therefore the aforementioned index-numbers in the notation $h_i(R,S,t)$, identifying the source 5 and the sensor 6. The function $h_i(R,S,t)$ is therefore simply a function of time representing the signal received by the sensor 6.

Figure 2:
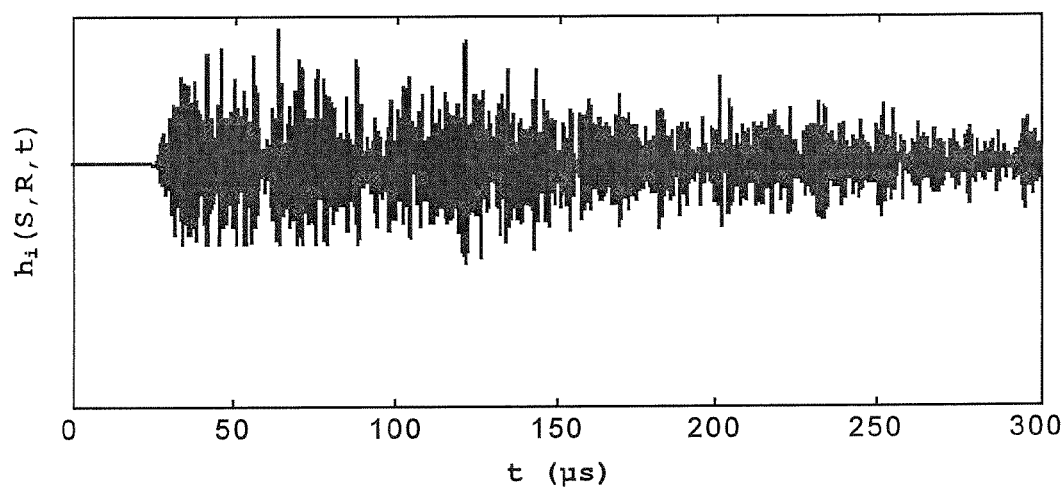
FIG. 2 is an example of an impulse response between a source and a sensor, used in the method.

Depending on the number of simultaneous channels on the acquisition equipment, these recordings are carried out one after the other or simultaneously for at least some of the sensors 6. The recordings may possibly be repeated so that they can be averaged, thus reducing the noise of the impulse responses recorded. FIG. 2 shows an example of an impulse response $h_i(R,S,t)$ obtained for a source-sensor pair 5, 6.

These measurements or recordings represent the ultrasonic digital fingerprint or signature of the medium on the date $t_i$.

The appearance of a defect U will thus lead to a modification of this fingerprint. The defect can be detected and located by comparing successive measurements, i.e. at least one before the appearance of the defect and at least one after the appearance of the defect. The measurements should therefore be recorded regularly, and advantageously as often as possible.

More specifically, the implementation of the method can comprise for example the following steps in succession:

During a first initialisation step of the method, a first set of measurements is carried out for example on the date t=0. The impulse responses from the first set of measurements are annotated $h_{ref}(R,S,t)=h_0(R,S,t)$.

Optionally, a mean of N impulse responses $h_j(R,S,t)$ is calculated on dates $t_j$ prior to the date $t_i$. j is therefore a natural number such that $0<=j<i$.

The impulse response on the date $t_0$ or the mean of the impulse responses defined previously constitutes a reference fingerprint $h_{ref}(R,S,t)$ of the medium 1.

In a second step of the method, the impulse responses $h_i(R,S,t)$ of the ultrasonic wave between the sources 5 and the sensors 6 are acquired on the date $t_i$ as described above.

It must be noted that the date $t_i$ of this acquisition can be carried out at several seconds, minutes, hours or days after the previous date, whilst the impulse response $h_i(R,S,t)$ is a function of time t, which is sampled at a high sampling frequency. If the wave is an ultrasonic wave, for example 500 kHz, the sampling frequency of the signal can be higher than the frequency of the wave, i.e. 1,000 kHz. The impulse response recording time is for example 0.3 ms (see FIG. 2), or less than 1 second.

The ultrasonic waves 2 are sensitive to global environmental variations in the medium, such as temperature, stresses, etc. The subject-matter of the method is to detect the appearance of localised defects U from local variations. These global variations can therefore disturb the detection of local variations, which is why it can be advantageous to correct the measurements of the impulse responses $h_i(R,S,t)$ to eliminate or at least reduce the effect of the global variations.

In a third step of the method, the impulse responses $h_i(R,S,t)$ are therefore optionally corrected by replacing them with corrected impulse responses $h_i(R,S,t(1-\epsilon))$, where $\epsilon$ is a temporal expansion coefficient that maximises the following correlation coefficient:

$$CC(\varepsilon) = \frac{\int h_i(R, S, t(1-\varepsilon)) \cdot h_{ref}(R, S, t) \cdot dt}{\sqrt{\int h_i^2(R, S, t) \cdot dt \cdot \int h_{ref}^2(R, S, t) \cdot dt}}, \quad (1)$$

the previous integrals being carried out on the entire signal of the impulse response $h_i(R,S,t)$.

The corrected impulse responses are advantageously re-sampled and interpolated so that they are sampled at the same instant in time as the uncorrected impulse responses $h_i(R,S,t)$, in such a way that the subsequent calculations are carried out in an identical manner.

In a fourth step of the method, a decorrelation coefficient $K_i(S,R,t)$ between the impulse response $h_i(R,S,t)$ on the date $t_i$ and the reference impulse responses $h_{ref}(R,S,t)$ is calculated, to compare the ultrasonic digital fingerprints, and which expresses the disturbance of the wave linked to the appearance of the defect U.

For example, for each source-sensor pair 5, 6, we have:

$$K_i(S, R, t) = 1 - \frac{\int_{t-T/2}^{t-T/2} h_i(R, S, t) \cdot h_{ref}(R, S, t) \cdot dt}{\sqrt{\int_{t-T/2}^{t+T/2} h_i^2(R, S, t) \cdot dt \cdot \int_{t-T/2}^{t+T/2} h_{ref}^2(R, S, t)}} \quad (2)$$

Where T is a temporal parameter, such that between t−T/2 and t+T/2, there are several oscillations in the impulse response $h_i(R,S,t)$. In particular, it may be worth noting that there are more than 10 oscillations around dynamic zero in this impulse response.

If there is no difference between the ultrasonic digital fingerprints, the decorrelation coefficient $K_i(S,R,t)$ is zero.

Differences between the ultrasonic digital fingerprints will generate a decorrelation coefficient $K_i(S,R,t)$ greater than zero.

If a defect appears in the medium, then the ultrasonic digital fingerprints will progressively decorrelate and the decorrelation coefficient $K_i(S,R,t)$ will increase.

If the fingerprints are random and independent of each other, the decorrelation coefficient $K_i(S,R,t)$ is then maximal and takes the value 1.

In a fifth step of the method, a probability of exploration $P(S,R,t,x) \cdot dx$ of a position x (to within dx) in the medium 1 by the ultrasonic wave, leaving from the source 5 and arriving at the sensor 6, after a time t, is calculated by the following integral:

$$P(S, R, t, x) \cdot dx = \int_0^t \frac{g(x_S, x, u) \cdot g(x, x_R, t-u)}{g(x_S, x_R, t)} \cdot du \quad (3)$$

Where $g(x_S,x,u)$ is the transport probability of the ultrasonic wave which, leaving the source 5 at time zero, arrives at position x after a time u, $g(x,x_R,t-u)$ is the transport probability of the ultrasonic wave which, leaving position x at time zero, arrives at the sensor 6 after a time t−u, $g(x_S,x_R,t)$ is the transport probability of the ultrasonic wave which, leaving the source 5 at time zero, arrives at the sensor 6 after a time t.

The probability function g corresponds to an intensity of the transmitted wave. This probability function g can be estimated in case a sensor 6 is present at position x ($x=x_R$), by the envelope of the impulse response $h_i(R,S,t)$:

$$g(x_R,x_s,t) \approx \text{envelope}(h_i^2(R,S,t)),$$

the envelope of this signal can be calculated by the absolute value of its Hilbert transform.

However, in order to calculate the probability of exploration $P(S,R,t,x)$ of the position x, it is necessary to calculate the probability function g at all points of the medium of position x, particularly at points where there is neither a source 5 nor a sensor 6.

In practice, complete knowledge of the probability function g is therefore difficult. This is why the probability function g is often calculated digitally by a model of the medium 1, into which is incorporated knowledge of, for example:

the geometry of the medium 1, the value of the scattering coefficient D of the wave in the medium 1, it being possible to estimate this scattering coefficient D by measurements on said medium, and parameters of the medium boundaries conditions, on its periphery or edges 3; and in particular absorption coefficients, of partial or total reflection, etc.

A first variant in order to simulate the model of the medium 1 is to solve a scattering equation of the type:

$$\frac{\partial g}{\partial t} = D \cdot \nabla^2 g$$

Where
g(x,t) is a quantity representing a wave, and
D is a scattering coefficient.

A second variant in order to simulate the model of the medium 1 is to solve a Paasschens equation.

Such an approach is more complex and produces more accurate results. Reference must be made to the following publication for its implementation: Paasschens, J. "Solution of the time-dependent Boltzmann equation", Phys. Rev. E, 1997, 56, 1135-1141.

A third variant in order to simulate the model of the medium 1 is to solve a radiative transfer equation.

Such an approach is even more complex and gives even more accurate results. Reference must be made for its implementation to the book by Chandrasekhar, S., "Radiative Transfer", Oxford University Press, 1950, and the publication by Margerin, L., Campillo, M. and Van Tiggelen, B. "Monte Carlo simulation of multiple scattering of elastic waves", J. Geophys. Res., 2000, 105, 7873-7892.

The calculation of the decorrelation coefficients $K_i(S,R,t)$ for each source-receiver pair 5, 6 gives an approximate value of the probability of exploration $P(S,R,t,x) \cdot dx$ of a position x by the ultrasonic wave.

In a sixth step of the method, an error function $e_i(S,R,x)$ is then calculated for each source-sensor pair 5, 6:

$$e_i(S, R, x) = F\left(\frac{K_i(S, R, t) - P(S, R, t, x)}{\sigma}\right)$$

where
F is a positive, even and decreasing function between 0 and $+\infty$.

This function can for example be approximated by a Gaussian distribution law using the following formula:

$$e_i(S, R, x) = \frac{1}{\sqrt{2 \cdot \pi} \cdot \sigma} \cdot e^{-\frac{[K_i(S,R,t)-P(S,R,t,x)]^2}{2 \cdot \sigma^2}}$$

Where
σ is the assumed maximum error,
$K_i$ is the decorrelation coefficient calculated by the series of impulse response measurements, and
P is the probability of exploration of a position x by the ultrasonic wave, calculated theoretically.

The multiplier factor $$\frac{1}{\sqrt{2 \cdot \pi} \cdot \sigma}$$

can optionally be omitted from the calculations, as it only represents a scale constant.

Finally, in a seventh step of the method, the product p of at least some of the error functions $e_i$ of the source-sensor pairs 5, 6 is calculated:

$$p(i, x) = \prod_{S,R} e_i(S, R, x)$$

This product p(i,x) represents a map or image of the probability of the appearance of a defect at each position x on the date $t_i$.

The product p can optionally be normalised by dividing each value of p by Norm:

Norm=∫p(i,x)·dx, integral over all of the positions x of the medium.

Figure 3:
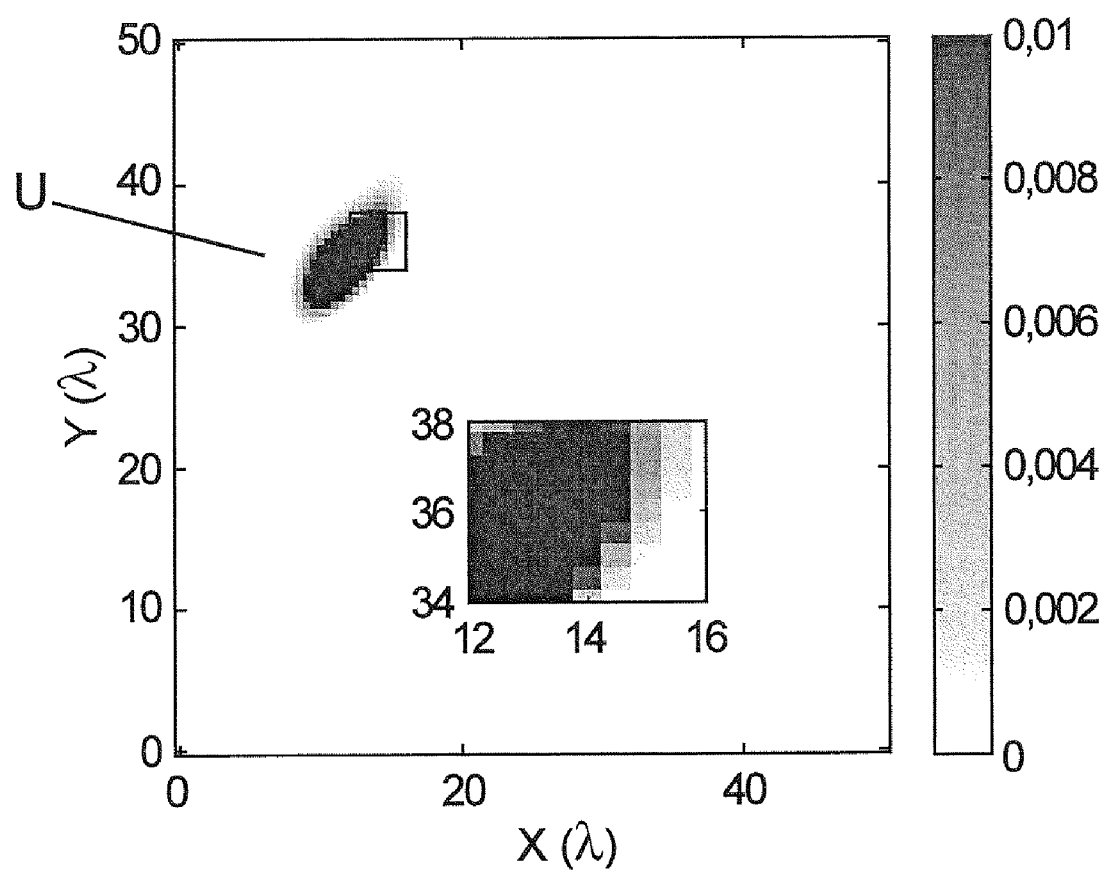
FIG. 3 is an example of a map of the probability of the appearance of a defect according to the method.

A two-dimensional example of such a map is given in FIG. 3, in which a scale ranging from white to black corresponds to a spatial probability density of the appearance of a defect ranging from 0 to 0.01 respectively. The unit is a probability density per wavelength squared, for detection on a surface. For detection within a volume, the unit will be a volume probability density per wavelength cubed. The defect U is pinpointed by a very dark mark centred on a position with the Cartesian coordinates (14, 35) in wavelengths λ.

FIG. 3 comprises a part showing an enlarged portion of the mark showing that the contrast between the mark and the background of the map is stark. The position of the defect U is therefore clearly defined in a region of the medium.

The invention claimed is:

1. A wave acquisition device physically adapted to execute a method for locating an appearance of a defect in a medium using a wave, said medium being equipped with:
    sources placed in said medium and adapted for emitting the wave in the medium,
    sensors placed in said medium and adapted for receiving said emitted wave, said method being characterised in that it comprises:
    an initialisation step in which reference impulse responses $h_{ref}(R,S,t)$ of the wave between the sources and the sensors are determined, then
    at least one defect detection step, in which:
    a) impulse responses $h_i(R,S,t)$ of the wave between the sources and the sensors are measured on a date $t_i$, i being a positive natural number,
    b) a decorrelation coefficient $K_i(S,R,t)$ between the impulse responses $h_i(R,S,t)$ on the date $t_i$ and the reference impulse responses $h_{ref}(R,S,t)$ is calculated,
    c) a probability of exploration $P(S,R,t,x)$ of a position x of the medium by the wave is calculated,
    d) an error function $e_i(S,R,x)$ for each source-sensor pair is calculated, and
    e) a product p(i,x) of at least some of the error functions $e_i(S,R,x)$ of said source-sensor pairs is calculated, by $$p(i, x) = \prod_{S,R} e_i(S, R, x),$$

said product p(i,x) representing a map of a probability of the appearance of a defect U at each position x.

2. The wave acquisition device according to claim 1, wherein the medium comprises heterogeneities and the wave is propagated in the medium according to a multiple scattering regime for which the wave interacts with more than one heterogeneity on its path.

3. The wave acquisition device according to claim 1 after step e), the product p(i,x) is normalised by dividing each value by Norm=∫p(i, x)·dx, integral over all of the positions x of the medium.

4. The wave acquisition device according to claim 1, wherein the reference impulse responses href(R,S,t) are determined by a mean of N impulse responses hi(R,S,t) on dates tj, j being a natural number such that 0<=j<i, and N being such that 1<=N<=i.

5. The wave acquisition device according to claim 1, wherein between steps a) and b), the measured impulse responses hi(R,S,t) are corrected by replacing them with corrected impulse responses hi(R,S,t(1-ϵ)), where ϵ is a temporal expansion coefficient that maximises the following correlation coefficient:

$$CC(\varepsilon) = \frac{\int h_i(R, S, t(1-\varepsilon)) \cdot h_{ref}(R, S, t) \cdot dt}{\sqrt{\int h_i^2(R, S, t) \cdot dt \cdot \int h_{ref}^2(R, S, t) \cdot dt}}.$$

6. The wave acquisition device according to claim 1, wherein, in which the decorrelation coefficient $K_i(S,R,t)$ is calculated using the following formula:

$$K_i(S, R, t) = 1 - \frac{\int_{t-T/2}^{t-T/2} h_i(R, S, t) \cdot h_{ref}(R, S, t) \cdot dt}{\sqrt{\int_{t-T/2}^{t+T/2} h_i^2(R, S, t) \cdot dt \cdot \int_{t-T/2}^{t+T/2} h_{ref}^2(R, S, t)}}$$

where
T is a temporal parameter, such that between t−T/2 and t+T/2, there are several oscillations in the impulse response $h_i(R,S,t)$.

7. The wave acquisition device according to claim 1, wherein the probability of exploration P(S,R,t,x) of the position x to within dx is calculated using the following formula:

$$P(S, R, t, x) \cdot dx = \int_0^t \frac{g(x_S, x, u) \cdot g(x, x_R, t-u)}{g(x_S, x_R, t)} \cdot du$$

Where
g($x_s$,x,u) is a transport probability of the wave which, leaving the source at time zero, arrives at position x after a time u,
g(x,$x_R$,t−u) is a transport probability of the wave which, leaving position x at time zero, arrives at the sensor after a time t−u,
g($x_s$,$x_R$,t) is the transport probability of the wave which, leaving the source at time zero, arrives at the sensor after a time t.

8. The wave acquisition device according to claim 1, wherein the error function ei(S,R,x) is calculated using the following formula:

$$e_i(S, R, x) = F\left(\frac{K_i(S, R, t) - P(S, R, t, x)}{\sigma}\right)$$

where
F is a positive, even and decreasing function between 0 and +∞,
σ is an assumed maximum error,
Ki is a decorrelation coefficient estimated by the impulse response measurements, and
P is a probability of exploration of the position x by the wave.

9. The wave acquisition device according to claim 1, wherein the error function ei(S,R,x) is calculated using the following formula:

$$e_i(S, R, x) = \frac{1}{\sqrt{2 \cdot \pi} \cdot \sigma} \cdot e^{-\frac{[K_i(S,R,t)-P(S,R,t,x)]^2}{2 \cdot \sigma^2}}$$

where:
σ is an assumed maximum error,
Ki is a decorrelation coefficient estimated by the impulse response measurements, and
P is a probability of exploration of the position x by the wave.

10. The wave acquisition device according to claim 1, wherein the medium is a composite building material.

11. The wave acquisition device according to claim 1, wherein the wave is an ultrasonic acoustic wave.

* * * * *